United States Patent [19]

Barcellos-Hoff

[11] Patent Number: 5,616,561
[45] Date of Patent: Apr. 1, 1997

[54] TGF-β ANTAGONISTS AS MITIGATORS OF RADIATION-INDUCED TISSUE DAMAGE

[75] Inventor: Mary H. Barcellos-Hoff, Oakland, Calif.

[73] Assignee: Regents of the University of California, Oakland, Calif.

[21] Appl. No.: 414,020

[22] Filed: Mar. 31, 1995

[51] Int. Cl.⁶ .................................................... A61K 38/00
[52] U.S. Cl. ............................................................ 514/13
[58] Field of Search ................................................. 514/13

[56] References Cited

U.S. PATENT DOCUMENTS 5,061,786  10/1991  Burnier et al. ............................ 514/13

Primary Examiner—James J. Seidleck
Assistant Examiner—John M. Cooney, Jr.
Attorney, Agent, or Firm—Kathleen DalBon; Paul R. Martin

[57] ABSTRACT

A method for treating tissue damage caused by radiation is described by use of a TGF-β antagonist, such as an anti-TGF-β antibody or a TGF-β latency associated protein. It is administered not more than a week after exposure, and is particularly useful in mitigating the side effects of breast cancer therapy.

21 Claims, No Drawings

TGF-β ANTAGONISTS AS MITIGATORS OF RADIATION-INDUCED TISSUE DAMAGE

The United States Government has certain rights to this invention pursuant to contract No. DE-AC03-76SF00098 between the U.S. Department of Energy and the University of California for the operation of Lawrence Berkeley Laboratory.

BACKGROUND

This invention relates to therapy for radiation induced tissue damage via antagonism of Transforming Growth Factor β (TGF-β).

Radiation therapy is currently one of the most useful methods of treating cancerous tumors. It has the unfortunate side effect, however, of damaging the normal tissue surrounding the tumor. This damage can include fibrosis, remodeling of the extracellular matrix, vascular damage, aberrant angiogenesis, pneuminitis, atherogenesis, osteonecrosis, mucositis, immunosuppression and functional impairment.

As discovered by the inventor, an early reaction to ionizing radiation is an activation of TGF-β, usually within one hour of exposure. (Barcellos-Hoff et al., "Transforming Growth Factor-β Activation in Irradiated Murine Mammary Gland,"*J. Clin. Invest.*, Vol. 93, pp. 892–899, 1994). The first tissue change, a restructuring of the extracellular matrix through collagen III induction, occurs within one day of the radiation exposure. (Barcellos-Hoff, "Radiation-induced Transforming Growth Factor β and Subsequent Extracellular Matrix Reorganization in Murine Mammary Gland," *Cancer Research*, Vol. 53, pp. 3880–3886, 1993). Fibrosis and other pathologic manifestations of the radiation-induced damage at higher than the cellular level can appear from three weeks to 6 to 12 months post-irradiation. These types of damage are particularly important in the liver, skin, lungs, gastrointestinal tract, kidneys, breast, testes, salivary gland, mucosa and brain.

Because of these radiation-induced side effects on the normal tissue surrounding the cancerous tumor being treated, less radiation can be used than might be optimal in tumor treatment. One researcher has been moved to say, "[w]ere it not for the presence of surrounding normal tissues, the total destruction of tumors by ionizing radiation would be readily achieved." (Murray, "Radiation-induced Fibrosis: the Structure/Function Relationship," *Scanning Microscopy*, Vol. 8, pp. 79–87, 1994). For example, hepatic veno-occlusive disease is a side effect of radiotherapy combined with bone marrow transplantation for neoplasia affected 15–50 percent of patients. It has a mortality rate of up to 50 percent. (Anscher et al., "Transforming Growth Factor β as a Predictor of Liver and Lung Fibrosis After Autologous Bone Marrow Transplantation for Advanced Breast Cancer," *N.E.J.M.*, 328:1592–1598, 1993).

There are certain patients particularly susceptible to radiation fibrosis because of compromising physical conditions such as systemic sclerosis, collagen vascular disease, systemic lupus erythematosus, and discoid lupus. The radiation treatment of these patients is even more severely limited. Accidental exposure to ionizing radiation in an industrial or research setting can, of course, also lead to fibrosis and the other types of radiation-induced tissue damage.

In order to minimize this radiation-induced damage to surrounding normal tissues, many techniques have been developed in an effort to limit this damage. Most revolve around limiting radiation to the lowest level effective for cancer treatment. Because there is a direct relationship between the amount of radiation and the effectiveness of the treatment, this method compromises the overall effectiveness of the treatment.

Radiation is often administered in as targeted a fashion as possible in an effort to limit damage to normal tissue. However, particularly when treating tissues deep in the body, this approach is not always possible since the radiation must go through layers of normal tissue to reach the cancerous tumor. Implanting a radiation source within the tumor is also used to limit damage to normal tissue. This method results in difficult to monitor dosages, and involves surgical risks. Furthermore, the radiation can still affect surrounding normal tissues.

Some types of fibrosis are currently treated with penicillamine. Use of penicillamine for post hoc treatment of radiation induced fibrosis is experimental. While penicillamine is being tested for anti-fibrosis therapy, the use of this agent does not address other types of radiation induced damage. Even when used in anti-fibrotic therapy, penicillamine has many adverse side effects.

There is a need for a therapeutic method to mitigate radiation induced tissue damage.

SUMMARY

The present invention is directed to a novel method for mitigating radiation induced tissue damage by administering a Transforming Growth Factor β (TGF-β) antagonist. It has been discovered by the inventor that by administering a TGF-β antagonist either locally or systemically before or shortly after radiation exposure, tissue damage is lessened.

It is an object of the invention to provide a therapeutic regimen to mitigate radiation-induced tissue damage.

It is a further object of the invention to provide a therapeutic regimen to mitigate radiation-induced tissue damage due to accidental or therapeutic radiation exposure.

It is an additional object of the invention to provide a therapeutic regimen to mitigate radiation-induced tissue damage allowing higher levels of therapeutic radiation exposure thereby increasing the effectiveness of radiation therapy for cancer treatment.

It is yet another object of the invention to provide a therapeutic regimen to mitigate radiation-induced tissue damage both for human patients and in animal husbandry.

The inventor has discovered that by administering a TGF-β antagonist, monoclonal antibody ID11.16, radiation-induced tissue damage is lessened. Although TGF-β activation has been shown to increase following radiation exposure, a causal connection between this activation and later pathologic effects of radiation on healthy tissue has not been demonstrated by researchers prior to the subject invention. One of the inventor's hypotheses for the mechanism for antagonism is that the antibody prevents the activated form of TGF-β from interacting with receptors. Other antagonists are proposed to antagonize through this or other mechanisms, including the prevention of TGF-β activation.

The inventor has shown that expression of Collagen III is among other physical changes abrogated by administration of TGF-β antagonist. These changes in the extracellular matrix specifically, are among the earliest detectable physical changes after radiation exposure.

The implications of this invention include use of more effective dosages of radiation therapy in cancer treatment without the concomitant concern of surrounding tissue damage, and prevention of tissue damage from accidental radiation exposure.

The clinical advantages of using optimal tumor treatment levels of radiation without concern for side effects cannot be underestimated. Radiation is a highly effective cancer treatment, but its side effects can be worse than the cancer. By use of the present invention, cancerous tumors can be treated without limiting treatment regimens due to these concerns.

While accidental exposures to ionizing radiation are uncommon in laboratory or nuclear facilities, they are extremely serious events when they occur. By providing for the first time a therapy which prevents the long term effects of the accidental exposure, the invention not only addresses the medical problems, but also mitigates the psychic stress on the victim of this type of accidental exposure.

These and other features, aspects, and advantages of the present invention will become better understood with reference to the following description and appended claims.

DETAILED DESCRIPTION OF THE INVENTION

The method for mitigating ionizing radiation-induced tissue damage according to the present invention comprises administering TGF-β antagonists to a patient (animal or human) exposed to the ionizing radiation either prior to, during, or after the exposure.

TGF-β Structure and Function

TGF-β is secreted into the extracellular matrix in a latent form. It is synthesized as a 390 amino acid precursor that is then cleaved into a carboxyl terminus and amino terminus. The 112 amino acid carboxyl terminus forms a homodimer which then undergoes posttranslational modifications. This modified homodimer is noncovalently associated with a dimer of the processed amino terminus. This processed amino terminus dimer is known as the latency associated peptide, or LAP. The TGF-β-LAP proform is secreted. Proteolytic cleavage of LAP results in activation.

TGF-β is believed to have a function in wound healing under normal conditions. TGF-β expression and activation are also correlated with radiation exposure. Transforming growth factor β (TGF-β) is actually comprised of a family of three closely related peptides that mediates myriad events during tissue homeostasis, growth and repair. The expression TGF-β is elevated in normal tissue exposed to radiation. Furthermore, the injection of TGF-β in some types of tissues triggers a fibrotic reaction.

TGF-β Antagonists

TGF-β antagonists which can be effectively employed in the subject invention include, among others, the latency associated peptide (LAP), and monoclonal antibodies, such as ID11.16, which can be raised against many possible epitopes of TGF-β. Other TGF-β antagonists include: aptamers, soluble receptors, and TGF-β binding proteins or portions thereof. Any antagonist to TGF-β, whether it prevents activation of TGF-β, or functions in some other way (for instance, by preventing receptor signaling) can be used.

Since there are three different, closely related forms of TGF-β, it is likely that antagonists may be identified that work preferentially or specifically on one of the forms of TGF-β. Virtually all of TGF-β research has been done on TGF-β(1). If the antagonism of one of the other forms is determined to more specifically mitigate radiation-induced tissue damage, the most advantageous antagonists can be chosen accordingly. Monoclonal antibodies raised against the distinguishing epitopes of the three forms would be likely candidates for form-specific antagonism.

The TGF-β antagonist useful in the subject inventive therapeutic method can be selected from the following: latency associated peptide (LAP), monoclonal antibodies, aptamers, soluble receptors, or TGF-β binding proteins or portions thereof. Preferably, the TGF-β antagonist is an anti-TGF-β antibody. More preferably, the TGF-β antagonist is a human recombinant anti-TGF-β antibody. Most preferably, the TGF-β antagonist is the anti-TGF-β monoclonal antibody ID11.16.

Therapy Administration

The inventive administration of the TGF-β antagonist can be localized to the region exposed to radiation damage, or the delivery of the TGF-β antagonist can be systemic.

Although no ill-effects have been found after systemic administration of ID11.16 in mice, it is generally accepted in medicine that targeted therapies are safer than systemic therapies. Indeed, this ability to target radiation to the area of the tumor is one of the advantages of radiation therapy over chemotherapy which is, by necessity, systemic.

In the case of TGF-β, the preference for localized administration of the TGF-β antagonist would come from TGF-β's normal role in wound healing. To be available for wound healing, TGF-β is constitutively expressed, albeit at low levels. It is this constitutive expression that causes the theoretical problem with systemic administration of the inventive TGF-β antagonist therapy.

The administration of the antagonist can be done using any appropriate method to administer a protein or nucleic acid therapeutic. If a patient sustained a wound before the antagonist had been fully catabolized by the body, there is a theoretical danger that healing would be compromised. Compared, however, to the danger of the cancerous tumor being treated with high levels of radiation, and the radiation-induced tissue damage to surrounding tissue, this theoretical risk may well be acceptable. Furthermore, there is evidence that the administration of TGF-β1 antagonists to a normal wound reduces scar tissue formation without compromising speed or effectiveness of healing.

Localized administration of TGF-β in the subject invention would minimize adverse effects or possible compromise of wound healing capacity in the patient. Localized methods such as intra-muscular injection, liposome delivery, or transdermal administration may be preferable in some cases to systemic methods.

Systemic methods such as intra-venous injection, intra-peritoneal injection or oral administration, could be provided with some of the advantages of localized administration by binding the antagonist to a tissue specific molecule. The tissue specific molecule, a hormone for instance, would then carry the antagonist to the appropriate tissue.

Dosage

In the present invention between 0.001 mg and 10 mg of antagonist per 100 grams body weight can be administered. Preferably between 0.01 mg and 5 mg per 100 grams body weight is administered in the subject invention. Most preferably between 0.1 mg and 1 mg of antagonist is administered per 100 grams body weight in the subject invention. This dosage regimen maximizes the therapeutic benefits of the subject invention while minimizing the amount of antagonist needed. Such an application minimizes costs as well as possible deleterious side effects.

Timing of Treatment

The administration of the TGF-β antagonist according to the subject invention can occur up to about a week before ionizing radiation exposure and about a week after ionizing radiation exposure depending on the antagonists' half-life in the body. In the case of antibodies, the half-life is at least several days. Elevated levels of activated TGF-β are seen for up to week following radiation exposure.

The antagonist must be administered early enough to bind to all the TGF-β and prevent the TGF-β from activating in response to the radiation exposure, but not so early as to be catabolized by the body. Preferably, the administration of the antagonist as per the subject invention is between 24 hours before and 24 hours after the exposure. Most preferably, the administration of the antagonist is between 5 hours before and 1 hour after exposure.

Tissues to be Treated

Virtually any tissue susceptible to radiation-induced tissue damage can gain protection by use of the inventive TGF-β antagonist treatment. Since natural TGF-β is systemic and virtually all tissues are susceptible to radiation-induced damage, any tissue would be appropriate for this treatment.

Breast tissue is an excellent candidate for receiving the benefit of the subject invention. Radiation-induced tissue damage can be a fatal side effect of over-exposure to radiation therapy. Typically, the fibrotic reaction common in normal breast tissue surrounding the cancerous tumor being treated with radiation therapy, undermines the cosmetic advantages of radiation therapy over surgical treatment. This disadvantage will lead many patients to elect a less effective or more dangerous treatment after radiation therapy.

Skin exposure is particularly common in accidental radiation exposure. It is an excellent candidate for the inventive therapy, especially as the TGF-β antagonist can be administered topically.

Other tissues that are susceptible to radiation-induced damage following accidental or therapeutic ionizing radiation exposure include: liver, lung, gastrointestinal tract, kidneys, testes, salivary gland, mucosa and brain. All of these tissues are appropriate for therapy with the present invention.

Type of Radiation Exposure

The invention is appropriate for use with any type of ionizing radiation exposure such as therapeutic or accidental X-ray, gamma ray, or beta particle exposure.

EXAMPLE 1

0.5 mg of the monoclonal anti-TGF-β antibody ID11.16 (obtained from Celtrix) was injected intra-peritoneally into 24 adult female BALB/c mice. 24 control mice were injected with the same amount of isotype-matched irrelevant antibody (KG7). 3 hours after the antibody injection, the mice were irradiated using $^{60}$Co gamma-rays at a dose rate of 0.35 Gy/min to a total dose of 5 Gy.

1 hour, or 1, 3, or 7 days later, 6 irradiated control animals which had not been treated with TGF-β antagonist, 6 experimental animals, and 6 non-irradiated, non-treated controls were sacrificed and the 4th pair of mammary glands were removed and embedded in OCT. No time points were taken for non-irradiated controls. The tissue blocks were frozen in a dry ice: ethanol bath and stored at −70° C. Sections 4 μm thick were obtained while sectioning at −30° to −35° C., the sections were immediately postfixed in methanol:acetone (1:1) at −20° C., air dried. and stored at −20° C.

Affinity-purified polyclonat goat antibodies to collagen III (Southern Biotechnology Associates, Birmingham, Ala.) were used at 5 ug/ml. Fluorescein-conjugated rabbit anti-goat IgG (Southern Biotechnology Associates) was used at 1:100 dilution.

Sections were removed from the freezer and placed directly in the supernatant of a solution of 0.5% casein in phosphate-buffered saline ($Na_2PO_4$:0.9% NaCl), pH 7.4 that had been stirred for 1 h at room temperature. After 30–60 min, each cover-slip was inverted on 25 μl of the primary antibody diluted working concentration in the blocking buffer. Incubation was at room temperature for 1–2 hours.

Sections were washed with 3 changes of phosphate-buffered saline containing 0.5% bovine serum albumin at room temperature and incubated with a 1:100 dilution of the fluorescein isothiocyanate-conjugated secondary antibody for 1 hour at room temperature. After a further 3 washes, the sections were mounted in Vectashield (Vector Laboratories, Palo Alto, Calif.). Sections were viewed using an Olympus microscope equipped with epifluorescence and photographed using Kodak film Trix 400. At least three independent staining experiments from two independent sets of irradiated or control samples were performed.

Results

Control animals which had not been treated with TGF-β antagonists showed Collagen III absence in the adipose stroma prior to irradiation. One hour and one day after irradiation, there was no change. By day 3, marked novel expression in the adipose stroma was evident. By day 7 there was striking resolution of adipose stroma Collagen III staining, (which was again comparable to pre-irradiation levels). This pattern of changing Collagen III expression was characterized as Collagen III induction.

The experimental animals which had been treated with TGF-β antagonist showed an abrogation of radiation-induced Collagen III induction. Visual comparison with the controls animals showed only mild expression of Collagen III in the adipose stroma at day 3 (as compared to marked expression in the untreated irradiated controls). At all time points, the immunofluorescence of the antagonist-treated animals was much more similar to non-irradiated animals than to irradiated and untreated animals.

EXAMPLE 2

The same protocol as outlined in Example 1 was performed, except the ID11.16 monoclonal anti-TGF-β antibody was administered via intra-venous injection. The same abrogation of Collagen III induction and similarity to non-irradiated animals was observed.

EXAMPLE 3

Following the protocol outlined in Example 1, dosages of ID11.16 of 0.1 mg, 0.25 mg and 1.0 mg were administered intra-peritoneally. No abrogation of Collagen III induction was observed with 0.1 mg dosage. That is, adipose stroma immunreactivity was marked. The 0.25 mg dosage of ID11.16 led to moderate adipose stroma Collagen III staining (minimal abrogation). The 1.0 mg dosage resulted in no adipose stroma Collagen III staining. This is complete abrogation of Collagen III induction and the same type of immunoreativity as is seen in unirradiated controls.

EXAMPLE 4

500 mg monoclonal anti-TGF-β antibody is administered intra-venously 2 hours before radiation therapy for human cancer patient. An increased dose of radiation is administered as compared to typical therapeutic radiation dosage. Despite increased therapeutic radiation exposure, the normal tissue surrounding the tumor does not become fibrotic or have other deleterious radiation-induced damage. Because of the increased level of therapeutic radiation exposure, treatment of the tumor is more effective than with the normal amount of radiation.

EXAMPLE 5

1 g monoclonal anti-TGF-β antibody is administered intra-venously as soon as possible and within one week of accidental exposure to ionizing radiation. Short and long-term tissue damage is significantly mitigated.

I claim:

1. A method for the mitigation of human tissue damage due to radiation exposure comprising the administration of a TGF-β antagonist.

2. The method of claim 1 wherein the TGF-β antagonist is a protein.

3. The method of claim 2 wherein the TGF-β antagonist is a TGF-β binding protein.

4. The method of claim 3 wherein the TGF-β antagonist is the TGF-β Latency Associated Protein (LAP).

5. The method of claim 3 wherein the TGF-β antagonist is a soluble receptor.

6. The method of claim 2 wherein the TGF-β antagonist is an anti-TGF-β antibody.

7. The method of claim 6 wherein the TGF-β antagonist is TGF-β neutralizing antibody ID11.16.

8. The method of claim 6 wherein the TGF-β antagonist is a human recombinant anti-TGF-β monoclonal antibody.

9. The method of claim 1 wherein the TGF-β antagonist is a nucleic acid.

10. The method of claim 1 wherein the administration of the antagonist is localized to the area affected by the tissue-damaging radiation.

11. The method of claim 10, wherein the antagonist is administered by a method selected from the group consisting of intra-peritonal administration, targeted delivery via tissue-specific carrier, local administration, and liposome delivery.

12. The method of claim 1 wherein the means of administration of the antagonist is systemic.

13. The method of claim 1 wherein the antagonist is administered by a method selected from the group consisting of intra-venous administration, intra-peritoneal administration, intra-muscular administration, liposome delivery, targeted delivery via tissue-specific carrier, oral administration, and trans-dermal administration.

14. The method of claim 1 wherein the tissue damage is to a tissue from the group consisting of: liver, lung, gastrointestinal tract, kidneys, breast, testes, salivary gland, mucosa and brain.

15. The method of claim 1 wherein the net weight of the antagonist used is between 0.001 mg and 10 mg per 100 grams body weight.

16. The method of claim 15 wherein the net weight of the antagonist used is between 0.01 mg and 5 mg per 100 grams body weight.

17. The method of claim 16 wherein the net weight of the antagonist used is between 0.1 mg and 1 mg per 100 grams body weight.

18. The method of claim 1 wherein the administration of the antagonist is delivered between not more than around 1 week before and not more than about 1 week after radiation treatment.

19. The method of claim 18 wherein the administration of the antagonist is delivered between not more than about 24 hours before and not more than about 24 hours after radiation treatment.

20. The method of claim 19, wherein the administration of the antagonist is delivered between not more than about 5 hours before and not more than about 1 hour after radiation treatment.

21. The method of claim 1 wherein 0.5 mg total protein weight per 100 g body weight of monoclonal antibody ID11.16 is administered intra-peritoneally 3 hours before the radiation exposure.

* * * * *